United States Patent
Thielsch et al.

(10) Patent No.: US 10,473,632 B2
(45) Date of Patent: Nov. 12, 2019

(54) METERING DEVICE WITH DEFINED ENABLED FLOW DIRECTION

(71) Applicant: Agilent Technologies, Inc., Santa Clara, CA (US)

(72) Inventors: Daniel Thielsch, Straubenhardt/Ottenhausen (DE); Thomas Ortmann, Straubenhardt/Ottenhausen (DE)

(73) Assignee: Agilent Technologies, Inc., Santa Clara, CA (US)

( * ) Notice: Subject to any disclaimer, the term of this patent is extended or adjusted under 35 U.S.C. 154(b) by 131 days.

(21) Appl. No.: 15/525,674

(22) PCT Filed: Nov. 10, 2014

(86) PCT No.: PCT/IB2014/002402
§ 371 (c)(1),
(2) Date: May 10, 2017

(87) PCT Pub. No.: WO2016/075503
PCT Pub. Date: May 19, 2016

(65) Prior Publication Data
US 2017/0322187 A1  Nov. 9, 2017

(51) Int. Cl.
*G01N 30/20* (2006.01)
*B01D 15/12* (2006.01)
(Continued)

(52) U.S. Cl.
CPC .......... *G01N 30/20* (2013.01); *B01D 15/12* (2013.01); *B01D 15/14* (2013.01); *B01D 15/163* (2013.01);
(Continued)

(58) Field of Classification Search
CPC ...................................................... G01N 30/20
(Continued)

(56) References Cited

U.S. PATENT DOCUMENTS 4,068,528 A  1/1978  Gundelfinger
4,444,066 A  4/1984  Ogle et al.
(Continued)

FOREIGN PATENT DOCUMENTS

EP  0321774 A2  6/1989
EP  2051071 A1  4/2009
(Continued)

OTHER PUBLICATIONS

International Search Report and Written Opinion from related Internation Application No. PCT/IB2014/002402.

*Primary Examiner* — John Fitzgerald
*Assistant Examiner* — Rodney T Frank

(57) ABSTRACT

A sample injector configured to introduce a sample fluid into a mobile phase, wherein the mobile phase is to be driven by a mobile phase drive through a separation unit for separating compounds of the sample fluid in the mobile phase, wherein the sample injector comprises a metering device being operable for displacing fluid and for intaking a metered amount of the sample fluid into the sample injector, an injector valve being switchable for operating the sample injector selectively in a sample intake mode in which the metering device is operable to intake the sample fluid from a sample container, or a separation mode in which intaken sample fluid is driven between the mobile phase drive and the separation unit for separating the compounds, and a flow direction controller configured for defining an enabled flow direction of fluid displaced by the metering device and for defining a disabled flow direction.

20 Claims, 5 Drawing Sheets

(51) Int. Cl.
  *B01D 15/14* (2006.01)
  *B01D 15/16* (2006.01)
  *B01D 15/26* (2006.01)
  *G01N 30/02* (2006.01)

(52) U.S. Cl.
  CPC ..... *B01D 15/265* (2013.01); *G01N 2030/027* (2013.01); *G01N 2030/207* (2013.01)

(58) Field of Classification Search
  USPC ...................................................... 73/61.55
  See application file for complete search history.

(56) References Cited

U.S. PATENT DOCUMENTS

| | | |
|---|---|---|
| 6,129,840 A | 10/2000 | Kitaoka |
| 2003/0098076 A1 | 5/2003 | Nichols |
| 2013/0067997 A1 | 3/2013 | Ebsen et al. |
| 2013/0336803 A1 | 12/2013 | Ruegenberg et al. |

FOREIGN PATENT DOCUMENTS

| | | |
|---|---|---|
| EP | 2345896 A1 | 7/2011 |
| EP | 1577012 B1 | 11/2014 |
| GB | 2486678 A | 6/2012 |
| JP | H0943217 A | 2/1997 |
| WO | 2010139359 A1 | 12/2010 |

METERING DEVICE WITH DEFINED ENABLED FLOW DIRECTION

RELATED APPLICATIONS

This application is the national stage under 35 U.S.C. 371 of International Application No. PCT/IB2014/002402, filed Nov. 10, 2014, titled "METERING DEVICE WITH DEFINED ENABLED FLOW DIRECTION", the entire contents of which are incorporated herein by reference.

BACKGROUND ART

The present invention relates to sample injectors, particularly for fluid separation apparatuses such as a high performance liquid chromatography application.

In high performance liquid chromatography (HPLC, see for instance http://en.wikipedia.org/wiki/HPLC), a liquid has to be provided usually at a very controlled flow rate (e.g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid with compounds to be separated is driven through a stationary phase (such as a chromatographic column), thus separating different compounds of the sample fluid.

Valves are commonly used in HPLC applications, for instance injection valves for introducing a liquid sample into a high pressure flowing stream of liquid, purge valves for positive displacement pumps, flow path switching valves, etc. Such valves used in HPLC applications are often multi-position rotary valves. Examples of multi-position rotary valves are disclosed in U.S. Pat. No. 4,068,528 A (two-position valves) or US 2003/0098076 A1 (multi-function rotary valves or random-access, dual, three-way, rotary switching valves).

Shear valves, which can be used in multi-way embodiments, are usually formed by a housing and a body defining a stepped cavity in which the rotor or seal is positioned. The housing contains at least two shear seal valve members positioned to be aligned with ports in the rotor (body) to establish communication between the shear seal means. Shear valves are usually provided as rotary valves (such as the aforementioned rotary valves) or translational valves (often also called sliding valves), such as disclosed in EP 0321774 A2.

In modern sample injectors, many functions need to be supported by a switchable valve. Conventional switchable valves and injector architectures may be inappropriate for such multi-function applications.

DISCLOSURE

It is an object of the invention to provide a precisely operating sample injector.

According to an embodiment of the present invention, a sample injector is provided which is configured to introduce a sample fluid (wherein a fluid, in the context of the present application, may denote a liquid and/or a gas, in particular optionally comprising solid particles) into a mobile phase, wherein the mobile phase is to be driven by a mobile phase drive through a separation unit for separating compounds of the sample fluid in the mobile phase, wherein the sample injector comprises a metering device being operable for displacing fluid and for intaking a metered amount of the sample fluid into the sample injector, an injector valve being switchable for operating the sample injector selectively in a sample intake mode in which the metering device is operable to intake the sample fluid from a sample container, or a separation mode in which intaken sample fluid is driven between the mobile phase drive and the separation unit for separating the compounds, and a flow direction controller configured for defining an enabled flow direction of fluid displaced by the metering device and for defining a disabled flow direction.

According to another embodiment of the present invention, a fluid separation apparatus for separating compounds of a sample fluid in a mobile phase is provided, wherein the fluid separation apparatus comprises a mobile phase drive, particularly a pumping system, configured to drive the mobile phase through the fluid separation apparatus, a sample injector having the above mentioned features and being configured to introduce the sample fluid into the mobile phase, and a separation unit, particularly a chromatographic column, configured for separating the compounds of the sample fluid in the mobile phase.

According to still another embodiment of the present invention, a method of operating a sample injector to introduce a sample fluid into a mobile phase is provided, wherein the mobile phase is to be driven by a mobile phase drive through a separation unit for separating compounds of the sample fluid in the mobile phase, wherein the method comprises switching an injector valve into a sample intake mode in which a metering device for displacing fluid is operated to intake a metered amount of a sample fluid from a sample container into the sample injector, subsequently switching the injector valve into a separation mode in which the intaken sample fluid is driven between the mobile phase drive and the separation unit for separating the compounds, and at least during the sample intake mode, enabling a flow of fluid displaced by the metering device along a defined flow direction and disabling a flow of fluid in an opposite flow direction.

According to an exemplary embodiment of the invention, a sample injector is provided, in which a sample fluid can first be intaken into a sample loop or the like of the injector device. For this purpose, it is for instance possible that a needle of the sample injector is driven out of a seat, in which it is normally located in a fluid-tight manner, and is immersed in sample fluid in a sample container (such as a vial). By the metering device, for instance by back driving a piston of the metering device within a piston chamber, sample fluid may be drawn from the sample container via the needle into the sample loop. During this sample intake procedure in the sample intake mode, the injector valve may ensure that a so-called main path between the mobile phase drive (such as a high pressure pump) and a separation unit (such as a chromatographic separation column) is fluidically decoupled from all components of the sample injector involved in the sample intake procedure. Subsequently, the injector valve may be switched into the separation mode in which the previously intaken sample fluid is injected between the mobile phase drive and the separation unit for carrying out a separation, for instance a chromatographic separation, of the sample fluid in its components. Advantageously, the metering device may be kept out of the sample separation path, i.e. may be out of fluid communication with the mobile phase drive and the separation unit, in the separation mode. The above workflow can be realized with a flow direction controller which can be considered as a mechanism which ensures that fluid is displaced by the metering device only along a respectively predefined fluid flow direction, whereas fluid flow in another fluid flow direction, in particular in an inverse fluid flow direction, is disabled. This has advantages in the sample intake mode, because driving the piston of the metering device in a backward direction may result in fluid being sucked into the piston chamber only from one of for instance two access ports of the metering device, i.e. from the side connected to the sample container, so that a defined fluid intake is possible. This fluid flow direction controller however has also advantages in the separation mode in which the metering device (when being outside of the main path) is free to carry out one or more additional tasks such as a precompression task for slightly increasing pressure around the metering device before the next switching operation, a decompression task for slightly decreasing pressure around the metering device before the next switching operation, or a seatback flush task, in which the flow direction controller also ensures a defined operation of the metering device and a displacement of fluid only in a predetermined manner. The flow direction controller therefore renders it possible to efficiently operate the sample injector in all operation modes without the necessity to locate the metering device within the flow path between mobile phase drive and separation unit. This reduces the dead volume contributed by the metering device itself in conventional approaches, since the metering device is now outside of the main path. Hence, the sample separation procedure can be rendered more accurate. Furthermore, in view of the precisely controlled fluid flow properties of the metering device, the separation procedure is properly reproducible. The flow direction controller furthermore makes is possible to flexibly operate the metering device and use it for various tasks so that the functionality of the sample injector can be improved as well.

In the following, further exemplary embodiments of the sample injector, the fluid separation apparatus and the method will be explained.

In one embodiment, the flow direction controller comprises one of a first flow direction valve and a flow restrictor arranged between the metering device and a first port (which may be connected to the sample loop and the needle in one switching state of the injector valve) of the injector valve. Hence, the definition of the enabled or disabled fluid flow direction may be accomplished by a first flow direction valve which is an additional fluidic valve located between a port of a sample injector and an access port of the metering device.

It should be said that the sample injector may for instance be a fluidic valve having a first valve member (such as a stator member) and has a second valve member (such as a rotor member) being movable (in particular rotatable) to one another. For instance, the first valve member may comprise a plurality of ports which may be fluidically coupled to the various components of the sample injector and the sample separation apparatus as a whole. The second valve member may comprise a plurality of grooves which are capable of fluidically connecting respective ones of the ports to one another in dependence of the relative orientation between the first valve member and the second valve member. The flow connection or fluid conduit between one of such ports of the injector valve on the one hand and the mentioned access port of the metering device on the other hand may now be modified by inserting the first flow direction valve which defines which of two possible flow directions (i.e. from injector valve to metering device, or from metering device to injector valve) is enabled and which is disabled. This may allow to prevent undesired backflow of fluid in an operation mode in which fluid shall be handled on another access port of the metering device.

In one embodiment, the flow direction controller comprises a second flow direction valve arranged between the metering device and a second port (which may be connected to the seat in one switching state of the injector valve) of the injector valve. By providing an additional second flow direction valve between the before mentioned other access port of the metering device and the injector valve both fluid conduits between the two opposing access ports of the metering device may be precisely controlled in terms of fluid flow enabling and fluid flow disabling.

In one embodiment, at least one of the first flow direction valve and the second flow direction valve is configured as a passive valve, in particular a non-return valve, more particularly a non-return spherical valve. By configuring any of the flow direction valves as a passive valve which is switched automatically by the fluid displaced by the metering device, a very simple construction of the flow direction valve or valves is possible. In other words, no control unit is required for switching these simply constructed flow direction valves in accordance with a desired switching scheme. The flow direction valves may be configured as small and lightweight non-return valves enabling flow in one direction and disabling flow in the opposite direction. For example, this may be accomplished by a ball valve. It should however be said that it is possible in one embodiment that two flow direction valves are provided which are both configured as ball valves. Alternatively, it is also possible that one of the ball valves is substituted by a flow restriction (such as a locally narrowed conduit section) or the like which limits flow between one of the access ports of the metering device and the respective port of the injector valve.

In one embodiment, the metering device comprises a piston movable in the piston chamber for displacing fluid, wherein piston backward motion enables fluid flow through the first flow direction valve while disabling fluid flow through the second flow direction valve, and piston forward motion enables fluid flow through the second fluid direction valve while disabling fluid flow through the first flow direction valve. Thus, in the described embodiment, piston operation which is anyway required for fluid displacement in terms of operating the sample injector also automatically switches the flow direction valves in the desired way. This allows to construct a sample injector with a compact and simple design.

In one embodiment, at least one of the first flow direction valve and the second flow direction valve is one of a valve biased into a fluid disabling mode by a biasing element, in particular one of a biasing weight and a biasing spring, more particularly one of a helical spring and a flat spring. With such a biasing element it is possible to keep the respective flow direction valve in a normally closed state, i.e. in a state in which it is closed in the absence of piston movement of the metering device. Hence, only piston movement then allows to overcome this default normally closed condition so that a save prevention of undesired fluid flow can be accomplished. One option is to configure the biasing element as a weight acting on a movable element of the respective flow direction valve. In such an embodiment, the respective flow direction valve should be oriented in such a way that the force of gravity can appropriately act on the biasing weight to accomplish the desired biasing function. Alternatively, a biasing spring may be used allowing to orient the respective flow direction valve in a desired way regardless of its relation to the force of gravity. In particular when using a flat spring, the respective flow direction valve may be embodied with a small size and with a pronounced capability of withstanding high pressure values of for instance up to 1200 bar or more, as may occur in modern liquid chromatography applications.

In one embodiment, the flow direction controller comprises a control unit configured for controlling a switching state of at least one of the first flow direction valve and the second flow direction valve to thereby define at least one of the enabled flow direction and the disabled flow direction. As an alternative to the before mentioned described passive embodiments of the flow direction valves, it is also possible to configure one or both of them as an actively controlled valve, i.e. a controllable switch. For this purpose, a control unit (such as a processor, for instance a microprocessor, or a CPU, central processing unit) may be provided which controls the respective flow direction valve to be switched into a closed state or an open state, allowing to flexibly adjust even sophisticated valve switching procedures. For example, such actively controllable flow direction valves may allow both of them to be temporarily in a flow enablement mode, both of them to be temporarily in a flow disablement mode, or one of them in a flow enablement mode and the other one in a flow disablement mode.

In one embodiment, the first flow direction valve and the second flow direction valve are configured so that, while one of them is in a fluid flow disabling mode, the other one is in a fluid flow enabling mode. Thus, it is possible to provide the flow direction valves so that, at each time, one of them allows a fluid flow through it and the other one disables a fluid flow through it. In a particularly preferred embodiment, when both of the flow direction valves are configured as passive non-return valves, they may be oriented antiparallel to one another which means that, when the piston of the metering device moves in one direction (i.e. forwardly or backwardly) at each time one of the passive non-return flow direction valves is on and the other one is off.

In one embodiment, in the separation mode, the first flow direction valve and the second flow direction valve are fluidically coupled to one another via the injector valve. Thus, while the injected sample fluid is separated between the mobile phase drive (such as a high pressure pump, for instance a pump displacing fluid with a pressure of up to 1200 bar or more), an annular flow path may be constituted by the metering device, the two flow direction valves, to ports and a corresponding groove of the injector valve, as well as of connected fluidic conduits. In this operation mode, a precompression or a decompression within this closed or annular flow path is enabled by forwardly or backwardly moving the piston of the metering device.

In one embodiment, the metering device is configured for depressurizing a fluidic path in which the metering device is located before switching into the sample intake mode. Such a depressurizing is useful when the pressure within the described flow path is still relatively high in view of a previous connection to the main flow path between mobile phase drive and separation unit. In order to prevent pressure shocks which may deteriorate or damage components of the sample injector and the whole sample separation apparatus, a depressurizing operation is appropriate.

In one embodiment, the metering device is configured for prepressurizing a fluidic path in which the metering device is located before switching into the separation mode. Hence, prepressurizing a portion of the sample injector which is subsequently switched between mobile phase drive and separation unit is possible. This includes the needle in the seat, the sample loop filled with the previously intaken sample fluid, a corresponding part of the injector valve and connected fluidic conduits.

In one embodiment, the injector valve is switchable for operating the sample injector in a mobile phase splitting mode in which mobile phase driven by the mobile phase drive is split at the injector valve to flow partially towards the separation unit and partially towards the metering device (at least one further partial flow towards another destination is possible as well). In such an additional mobile phase splitting mode, the mobile phase conducted by the mobile phase drive may be split in accordance with a predefinable ratio between the metering device and the main flow path. For instance, when fluid in accordance with a flow rate of 500 µl/min is displaced by the mobile phase drive, a partial flow of 400 µl/min may be directed towards the separation unit and a remaining partial flow of 100 µl/min may be directed towards the metering device. This ratio may be defined by a corresponding backward motion velocity of the piston of the metering device during splitting. In such an embodiment, cooperation between mobile phase drive and metering device is possible and advantageous. In such a split flow mode, the metering device may contribute to the precise adjustment of a desired flow in the main path, and at the same time the fluid directed towards the metering device may be used for rinsing, flushing or cleaning.

In one embodiment, the metering device is outside of a flow path between the mobile phase drive and the separation unit in both the separation mode and the sample intake mode. In a further embodiment, the metering device is outside the main path in each operation mode of the sample injector and the sample separation apparatus. Thus, the dead volume within the flow path is maintained small, since the interior volume of the metering device does not contribute to this dead volume any longer when the metering device is outside the main path.

In one embodiment, the sample injector comprises a needle which is movable into a sample container (containing sample fluid) in the sample intake mode, and which is movable into a seat (to establish a fluid-tight connection between needle and seat) in fluid communication with the injector valve in the sample separation mode. For moving the needle between sample container and seat, a robot or the like may be used. Directly connected to the needle, a certain part of the fluidic conduit connecting the needle to the injector valve may be provided for temporarily storing intaken sample fluid, i.e. a so-called sample loop.

In one embodiment, the metering device is controllable for moving a piston of the metering device multiple times forwardly and backwardly in an alternating manner (so that the piston reciprocates) in the sample intake mode while the needle remains in the sample container to thereby intake multiple quantities (in particular one during each backward motion of the piston) of the sample fluid during the reciprocating motion of the piston. Such a multi-draw mode becomes also possible in view of the configuration of the metering device with the flow direction controller. Since the flow direction controller, in one embodiment, allows a fluid flow always only in one direction while disabling it in the opposite direction, the piston in the metering device may be moved alternatively between a forward displacement and a backward displacement, wherein during each backward displacement additional sample fluid is drawn into the sample loop which is not moved backwardly during a subsequent forward motion of the piston (when the flow direction controller comprises a correspondingly oriented non-return valve). This allows to inject even larger amounts of sample fluid into the main path which amounts can be larger than a maximum amount of fluid displaced by the metering device during one stroke.

In one embodiment, the metering device is controllable for moving a piston of the metering device forwardly when the needle is out of fluid communication with the mobile phase drive, in particular when the needle is outside of the seat, to thereby backflush the seat. Hence, when the needle is out of the seat and the piston of the metering device moves forwardly, mobile phase is displaced which can be guided through one of two flow direction valves (i.e. the one which is open when the piston moves forwardly) and from there through the open seat. This flushes the seat for preventing carryover of sample fluid between different operation modes.

In one embodiment, the sample injector comprises a further needle which is movable into a sample container for intaking further sample fluid while other sample fluid previously intaken via the other needle is separated in the separation mode, and which further needle is movable into a further seat in fluid communication with the injector valve for driving the intaken further sample fluid between the mobile phase drive and the separation unit for separation so that while one of the needle and the further needle is arranged in a fluidic path between the mobile phase drive and the separation unit, the respective other needle is operable for intaking sample fluid. Hence, the configuration of the sample injector with the flow direction controller and the correspondingly operating metering device is capable to serve two needle-seat arrangements with one injector valve and one metering device. In this configuration, at a time one of the needle-seat arrangements is operated for intaking fluid while previously intaking sample fluid of the other needle-seat arrangement is presently within the main path between mobile phase drive and separation unit. Therefore, a highly efficient sample separation apparatus is provided which allows to be operated with a high throughput.

Embodiments of the present invention might be embodied based on most conventionally available HPLC systems, such as the Agilent 1200 Series Rapid Resolution LC system or the Agilent 1100 HPLC series (both provided by the applicant Agilent Technologies—see www.agilent.com—which shall be incorporated herein by reference).

One embodiment comprises a pumping apparatus as the mobile phase drive having a piston for reciprocation in a pump working chamber to compress liquid in the pump working chamber to a high pressure at which compressibility of the liquid becomes noticeable.

The separation unit preferably comprises a chromatographic column (see for instance http://en.wikipedia.org/wiki/Column_chromatography) providing the stationary phase. The column might be a glass or steel tube (for instance with a diameter from 50 µm to 5 mm and a length of 1 cm to 1 m) or a microfluidic column (as disclosed for instance in EP 1577012 or the Agilent 1200 Series HPLC-Chip/MS System provided by the applicant Agilent Technologies, see for instance http://www.chem.agilent.com/Scripts/PDS.asp?lPage=38308). For example, a slurry can be prepared with a powder of the stationary phase and then poured and pressed into the column. The individual components are retained by the stationary phase differently and separate from each other while they are propagating at different speeds through the column with the eluent. At the end of the column they elute one at a time. During the entire chromatography process the eluent might be also collected in a series of fractions. The stationary phase or adsorbent in column chromatography usually is a solid material. The most common stationary phase for column chromatography is silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface, though in EBA a fluidized bed is used.

The mobile phase (or eluent) can be either a pure solvent or a mixture of different solvents. It can be chosen for instance to minimize the retention of the compounds of interest and/or the amount of mobile phase to run the chromatography. The mobile phase can also be chosen so that the different compounds can be separated effectively. The mobile phase might comprise an organic solvent like for instance methanol or acetonitrile, often diluted with water. For gradient operation water and organic are delivered in separate bottles, from which the gradient pump delivers a programmed blend to the system. Other commonly used solvents may be isopropanol, tetrahydrofuran (THF), hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The pressure in the mobile phase might range from 2-200 MPa (20 to 2000 bar), in particular 10-150 MPa (100 to 1500 bar), and more particularly 50-120 MPa (500 to 1200 bar).

The HPLC system may further comprise a detector for detecting separated compounds of the sample fluid, a fractionating unit for outputting separated compounds of the sample fluid, or any combination thereof. Further details of HPLC system are disclosed with respect to the Agilent 1200 Series Rapid Resolution LC system or the Agilent 1100 HPLC series, both provided by the applicant Agilent Technologies, as described at the website www.agilent.com.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

Figure 1:
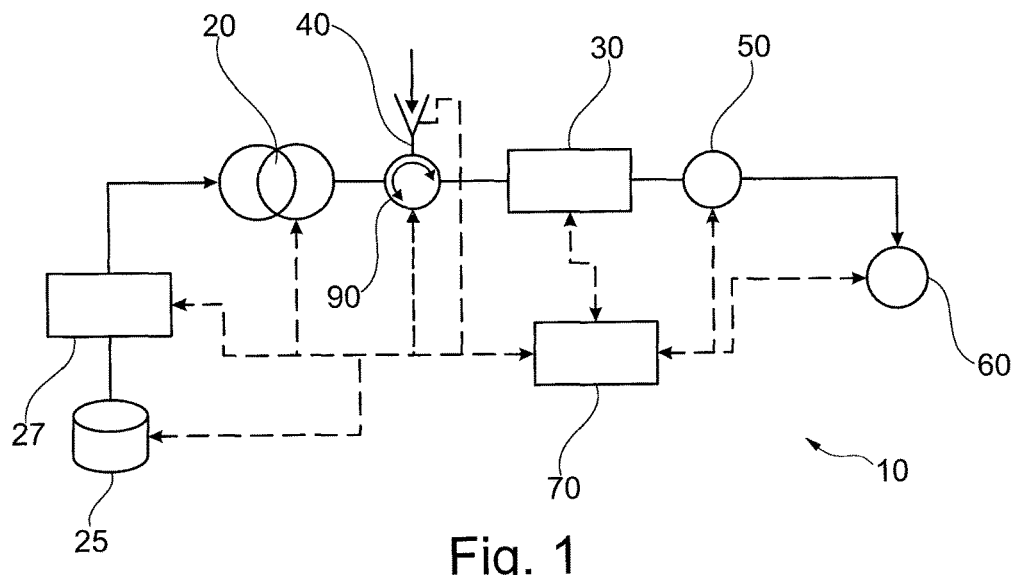
FIG. 1 shows a fluid separation system, in accordance with embodiments of the present invention, for instance used in high performance liquid chromatography (HPLC).

The illustration in the drawing is schematic.

DETAILED DESCRIPTION

Before describing the figures in further detail, some basic considerations of the present inventors will be summarized based on which exemplary embodiments have been developed.

According to exemplary embodiment of the invention, a metering device is configured so as to be located out of a flow path with the capability for seat-backflush and multi draw. A corresponding embodiment of the invention is related to a configuration in which the metering device is positioned out of the flow path but using current fresh solvent of the flow path to purge. Advantageously, a metering device used outside of a flow path is capable of reducing the dead volume. Moreover, the metering device can automatically be primed with current solvent. With such an architecture, it is additionally possible that the metering device has additional functionality by the usage of two ball valves. A so-called metering home procedure, during which a piston of the metering device is moved back into a home position (i.e. a predetermined position within the piston chamber), can be used for backflush of the seat. A metering device according to an exemplary embodiment may also be configured with a full compress and decompress capability.

In order to obtain these advantages, two additional high pressure ball valves (or any other appropriately configured flow direction controller) may be implemented, one upstream (or connected to a flow inlet access port of the metering device) and the other downstream (or connected to a flow outlet access port of the metering device) of the metering device. By the usage of two additional high pressure ball valves or the like, the metering device can be used outside the flow path. Also it can be primed with current solvent (out of loop capillary with a special procedure). There is no need for an additional flush pump. This setup allows to operate the system with the metering device outside flow path to reduce dead volume. In combination of a metering device with a front sealed piston the needed volume for priming is small. In addition a seat backflush capability is given—during the metering home movement of the piston. A real multi draw is realizable during which the needle can remain in the sample during the multiple piston movement for multi draw. With such an architecture, pressurization and depressurization are feasible. Only one high pressure valve pod and two high pressure ball valves are sufficient.

Referring now in greater detail to the drawings, FIG. 1 depicts a general schematic of a fluid separation system 10. A pump as a mobile phase drive 20 receives a mobile phase from a solvent supply 25, typically via a degasser 27, which degasses and thus reduces the amount of dissolved gases in the mobile phase. The mobile phase drive 20 drives the mobile phase through a separation unit 30 (such as a chromatographic column) comprising a stationary phase. A sampling unit or sample injector 40 (compare the detailed description of FIG. 2 to FIG. 10) can be provided between the mobile phase drive 20 and the separation unit 30 in order to subject or add (often referred to as sample introduction) a sample fluid into the mobile phase. The stationary phase of the separation unit 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the mobile phase drive 20, so that the mobile phase drive 20 already receives and pumps the mixed solvents as the mobile phase. Alternatively, the mobile phase drive 20 might be comprised of plural individual pumping units, with plural of the pumping units each receiving and pumping a different solvent or mixture, so that the mixing of the mobile phase (as received by the separation unit 30) occurs at high pressure and downstream of the mobile phase drive 20 (or as part thereof). The composition (mixture) of the mobile phase may be kept constant over time, the so called isocratic mode, or varied over time, the so called gradient mode.

A data processing unit or control unit 70, which can be a conventional PC or workstation, might be coupled (as indicated by the dotted arrows) to one or more of the devices in the fluid separation system 10 in order to receive information and/or control operation. For example, the control unit 70 might control operation of the mobile phase drive 20 (for instance setting control parameters) and receive therefrom information regarding the actual working conditions (such as output pressure, flow rate, etc. at an outlet of the pump 20). The control unit 70 might also control operation of the solvent supply 25 (for instance setting the solvent/s or solvent mixture to be supplied) and/or the degasser 27 (for instance setting control parameters such as vacuum level) and might receive therefrom information regarding the actual working conditions (such as solvent composition supplied over time, flow rate, vacuum level, etc.). The control unit 70 might further control operation of the sample injector 40 (for instance controlling sample injection or synchronization of sample injection with operating conditions of the mobile phase drive 20). The separation unit 30 might also be controlled by the control unit 70 (for instance selecting a specific flow path or column, setting operation temperature, etc.), and send in return information (for instance operating conditions) to the control unit 70. Accordingly, the detector 50 might be controlled by the control unit 70 (for instance with respect to spectral or wavelength settings, setting time constants, start/stop data acquisition), and send information (for instance about the detected sample compounds) to the control unit 70. The control unit 70 might also control operation of the fractionating unit 60 (for instance in conjunction with data received from the detector 50) and provide data back.

Reference numeral 90 schematically illustrates a switchable fluidic valve, which may also be denoted as injector valve, which is controllable for selectively enabling or disabling specific fluidic paths within fluid separation system 10. An example of the constitution of injector valve 90 and its integration in sample injector 40 will be explained in the following in more detail.

FIG. 2 to FIG. 5 show sample injector 40 according to an exemplary embodiment in different operation modes.

The sample injector 40 is configured to introduce a sample fluid into a mobile phase. The mobile phase is to be driven by mobile phase drive 20 through separation unit 30 for separating compounds of the sample fluid in the mobile phase. The sample injector 40 comprises a metering device 200 which is embodied as a piston pump with a piston 208 being mounted in a piston chamber 210 for reciprocating therein, i.e. moving forwardly or backwardly, to thereby displace fluid. The metering device 200 is configured for intaking a metered amount of the sample fluid into the sample injector 40.

The sample injector 40 furthermore comprises a flow direction controller 202 configured for defining an enabled flow direction of fluid displaced by the metering device 200 and for defining a disabled flow direction. The flow direction controller 202 comprises a first flow direction valve 204, configured as a passive non-return ball valve, arranged between the metering device 200 and a first port 3 of the injector valve 90. In addition to that, the flow direction controller 202 comprises a second flow direction valve 206, which is also embodied as a passive non-return ball valve, and which is arranged between the metering device 200 and a second port 4 of the injector valve 90. The flow direction valves 204, 206 are both actuated by fluid flowing through the conduits connected to the flow direction valve 204, 206 under the influence of piston movement of the metering device 200. In particular, forward motion of the piston 208 (see the arrow in FIG. 4) disables fluid flow through the first flow direction valve 204 while enabling fluid flow through the second flow direction valve 206. Correspondingly, piston backward motion (i.e. motion of the piston 208 antiparallel to the arrow in FIG. 4) disables fluid flow through the second flow direction valve 206 while enabling fluid flow through the first flow direction valve 204. Consequently, the first flow direction valve 204 and the second flow direction valve 206 are coupled via respective opposing access ports of the metering device 200 so that, under the influence of fluid displaced by the metering device 200, one of the flow direction valve 204, 206 is always in a fluid flow disabling mode, while the other one of the flow direction valves 204, 206 is at the same time in a fluid flow enabling mode.

Figure 5:
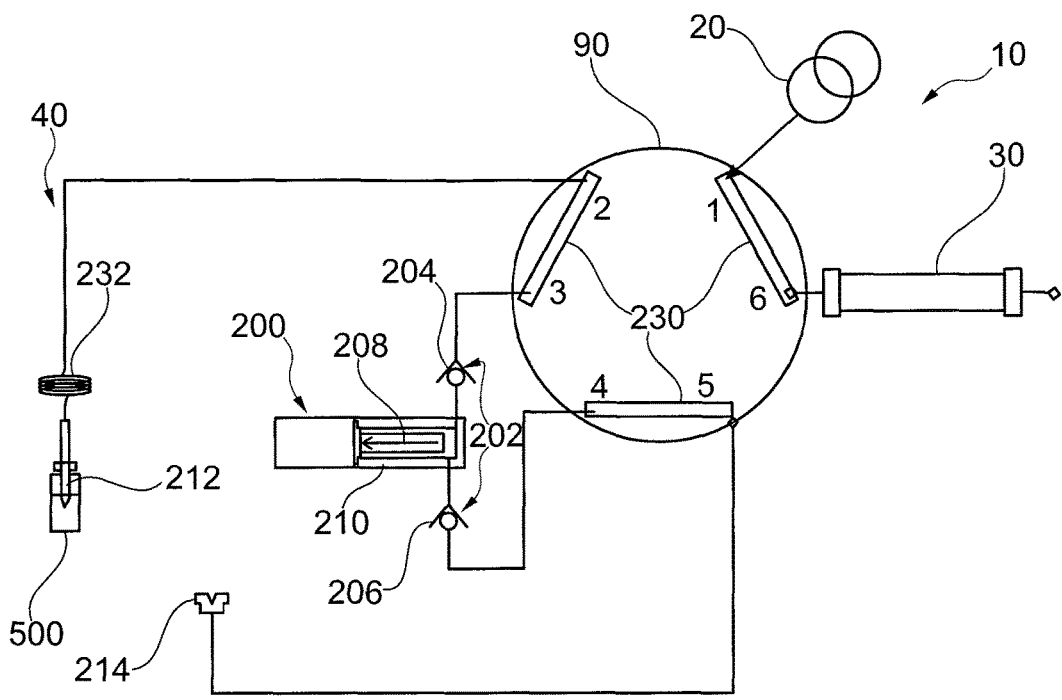
FIG. 5 shows the sample injector illustrated in FIG. 2 in another operating mode.

The sample injector 40 furthermore comprises a movable needle 212 (movable for instance by a robot, not shown) which is movable into a sample container 500 in a sample intake mode (see FIG. 5). Moreover, the needle 212 is movable into a seat 214 in fluid communication with the injector valve 90 in a sample separation mode (see FIG. 2). When the needle 212 is moved in the seal 214, the needle-seal arrangement provides a fluid-tight and pressure-resistant fluidic connection. When fluid is intaking from the sample container 500 through the needle 212, it can be temporarily accommodated in sample loop 232. The sample loop 232 is constituted by a part of the fluidic conduit between the needle 212 and port 2 of the injector valve 90 in which sample loop 232 a predefined volume of sample fluid intaken from a sample container 500 and to be injected between the mobile phase drive 20 and the separation unit 30 can be temporarily stored. Remaining fluidic conduits within the sample injector 40 can be filled with a mobile phase such as a predefined solvent composition.

The injector valve 90 comprises a plurality of ports (in the shown embodiment six ports denoted with 1 to 6) at which the various fluidic components are connected. Between these ports 1 to 6, a plurality of grooves 230 are arranged respectively bridging two or more of the ports. By moving two valve members (i.e. a rotor and a stator) of the injector valve 90 relative to one another, different coupling states of respective ones of the ports 1 to 6 by respective ones of the grooves 230 can be accomplished, thereby allowing to adjust different operation modes of the sample separation apparatus 10.

The injector valve 90 is switchable for operating the sample injector 40 in different operation modes. As can be taken from FIG. 2 to FIG. 5, the metering device 200 is always outside of a flow path between the mobile phase drive 20 and the separation unit 30, i.e. is outside of the main path, in each and every operation mode of the sample injector 40.

Figure 2:
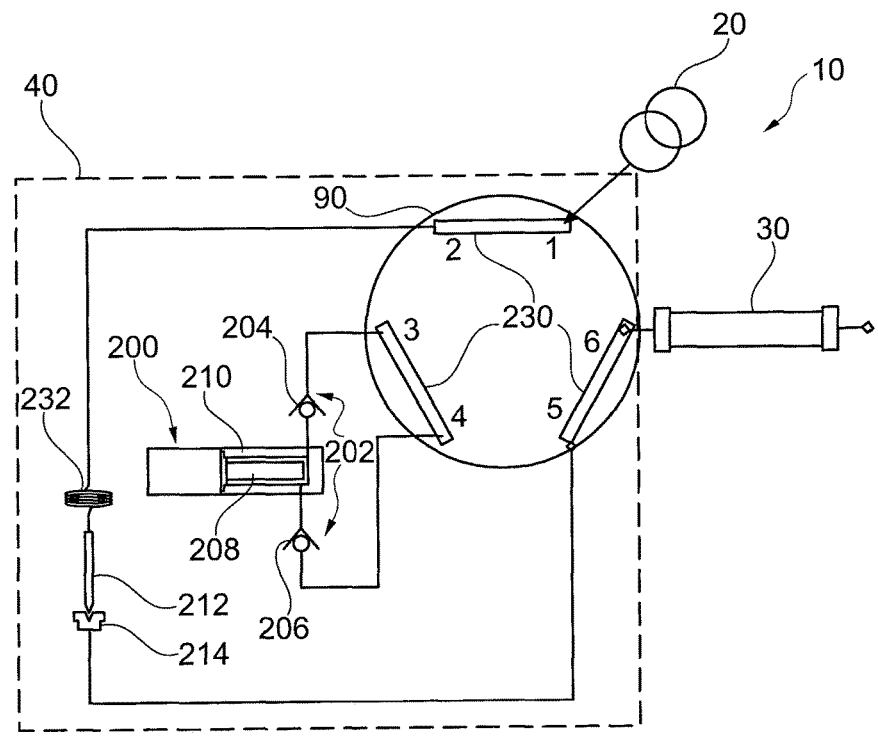
FIG. 2 shows a sample injector according to an exemplary embodiment in an operating mode.

As shown in FIG. 2, the injector valve 90 may switch the sample injector 40 in a separation mode in which intaken sample fluid, temporarily accommodated in the sample loop 232, is driven between the mobile phase drive 20 and the separation unit 30 for separating the compounds. In the separation mode, the first flow direction valve 204 and the second flow direction valve 206 are fluidically coupled to one another via the injector valve 90. According to FIG. 2, the sample injector 40 is in the mainpass, whereas the metering device 200 is out of this main path. Consequently, a pre-drawn sample fluid is injected in a flow path between the mobile phase drive 20 and the separation unit 30. Since the metering device 200 is outside of the main path, it is possible to depressurize the blocked metering device 200 in this operation mode. FIG. 2 hence shows the sample separation apparatus 10 in the sample separation mode in which the injector valve 90 assumes a corresponding switching state. In the separation mode, a flow path from the mobile phase drive 20 through port 1, a groove 230, port 2 of the injector valve 90, the sample loop 232, the needle 212, the seat 214, ports 5 and 6 as well as a further groove 230 of the injector valve 90 and the separation unit 30 is accomplished. Hence, sample fluid previously intaken in the sample loop 232 is separated in the separation unit 230 and mobile phase is pumped through the described flow path by the operation of the mobile phase drive 20. At the same time, an annular flow path is formed by the metering device 200, the two flow direction valves 204, 206, one groove 230 and corresponding ports 3 and 4 of the injector valve 90. By moving piston 208 of the metering device 200 forwardly in the configuration of FIG. 2, the annular fluidic path may be precompressed (i.e. brought to a higher pressure value), while back driving the piston 208 in the operation mode according to FIG. 2 allows to decompress this annular fluidic path (i.e. to reduce the pressure in this fluidic path).

Figure 3:
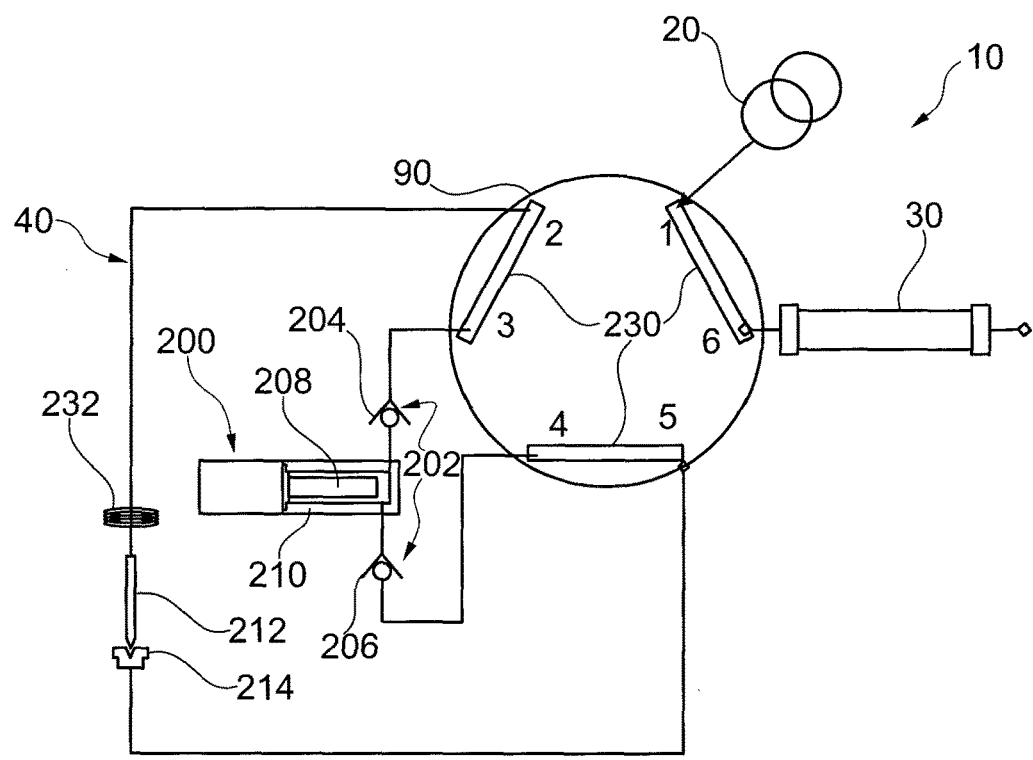
FIG. 3 shows the sample injector illustrated in FIG. 2 in another operating mode.

The injector valve 90 may also switch the sample injector 40 into a bypass mode as shown in FIG. 3 in which the mobile phase drive 20 may displace mobile phase through injector valve 90 towards the separation unit 30, while the metering device 200, the needle 212 and the seat 214 are fluidically coupled via the injector valve 90 and the flow direction controller 202 in an annular flow path. In the bypass mode according to FIG. 3, the metering device 200 is configured for depressurizing a fluidic path in which the metering device 200 is located. It is also possible in the bypass mode according to FIG. 3 that the metering device 200 is operated for prepressurizing a fluidic path in which the metering device 200 is located. The bypass mode can be accomplished by switching the injector valve 90 starting from the operation mode in FIG. 2 into the groove-port coupling state shown in FIG. 3. Now the mobile phase drive 20 is connected via ports 1 and 6 and a corresponding groove 230 of the injector valve 90 with the separation unit 30. Separately from this main path, the metering device 200 is a closed flow path via first flow direction valve 204, port 3, a groove 230, port 2, sample loop 232, needle 212, seat 214, port 5, a groove 230, port 4 and second flow direction valve 206.

Figure 4:
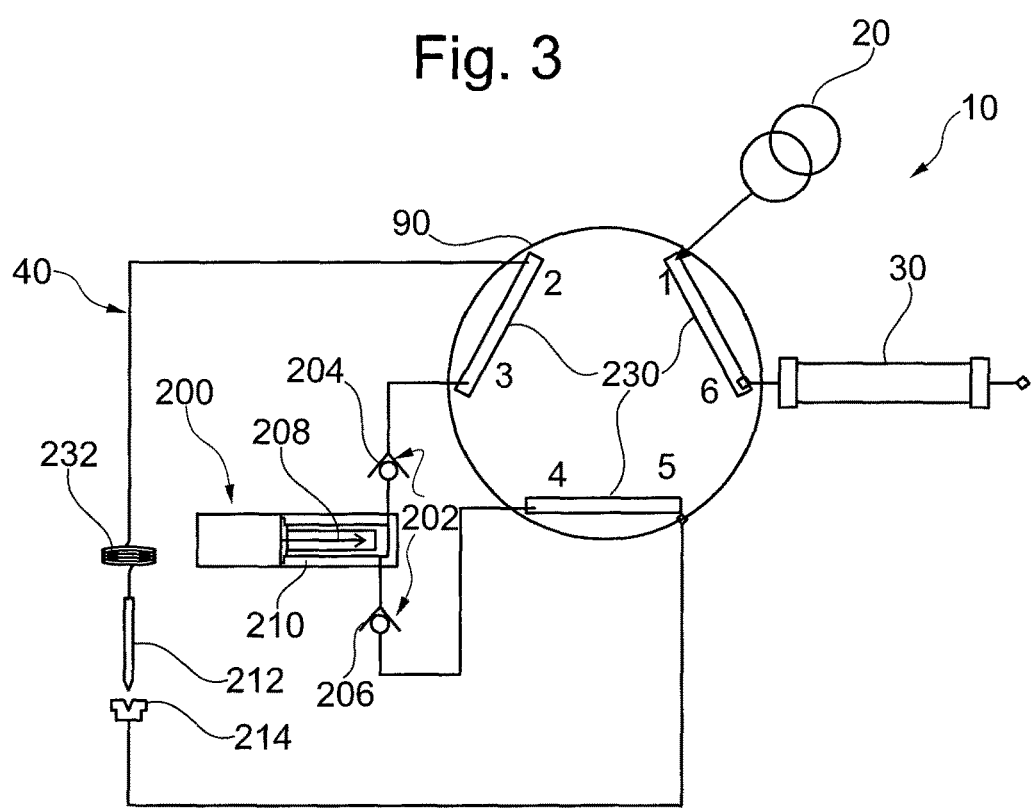
FIG. 4 shows the sample injector illustrated in FIG. 2 in another operating mode.

Referring to FIG. 4, a seat backflush mode is shown. In this operation mode, the main path between the mobile phase drive 20 and the separation unit 30 is still in a bypass configuration. The metering device 200 moves it is piston 208 forwardly towards a home position and thereby displaces fluid which will be forwarded through second flow direction valve 206, not through first flow direction valve 204, to flush the seat 214. According to FIG. 4, the metering device 200 can hence perform a metering home procedure resulting in seat-backflush.

For instance as shown in FIG. 5, the injector valve 90 may switch the sample injector 40 in a sample intake mode in which the metering device 200 is operable to intake the sample fluid from sample container 500 through needle 212 into sample loop 232. If relatively large volumes of sample fluid to be separated shall be handled, the metering device 200 is controllable for moving piston 208 of the metering device 200 multiple times forwardly and backwardly in the sample intake mode according to FIG. 5 while the needle 212 remains in the sample container 500 to thereby intake multiple quantities of the sample fluid during the multiple backward motions of the piston 208. However, and which has already been described referring to FIG. 4, it is also possible that the metering device 200 is controllable for moving piston 208 of the metering device 200 forwardly when the needle 212 is out of fluid communication with the mobile phase drive 20, in particular when the needle 212 is outside of the seat 214, to thereby backflush the seat 214. As can be taken from FIG. 5, the metering device 200 can draw sample. The metering device 200 can pressurize sample loop 232, needle 212, seat 214, and other fluidic members (such as valve grooves 230, capillaries coming from and getting to metering device 200, flow direction valves 204, 206 embodied as ball valves, etc.).

By a backward motion of piston 208 in the shown operation mode, as indicated by an arrow in FIG. 5, the sample fluid is drawn from the sample container 500 through the needle 212 into the sample loop 232 and mobile phase within the conduit between the needle 212 and the metering device 200 is guided via first flow direction valve 204 into the piston chamber 210 of the metering device 200. Via this backward motion of the piston 208 the second flow direction valve 206 is closed, i.e. disables fluid flow. When, in the operation mode shown in FIG. 5, piston 208 is moved forwardly, the first flow direction valve 204 closes and mobile phase is pumped from the metering device 200 through the second flow direction valve 206 through the seat 214 which is thereby back flushed.

Figure 6:
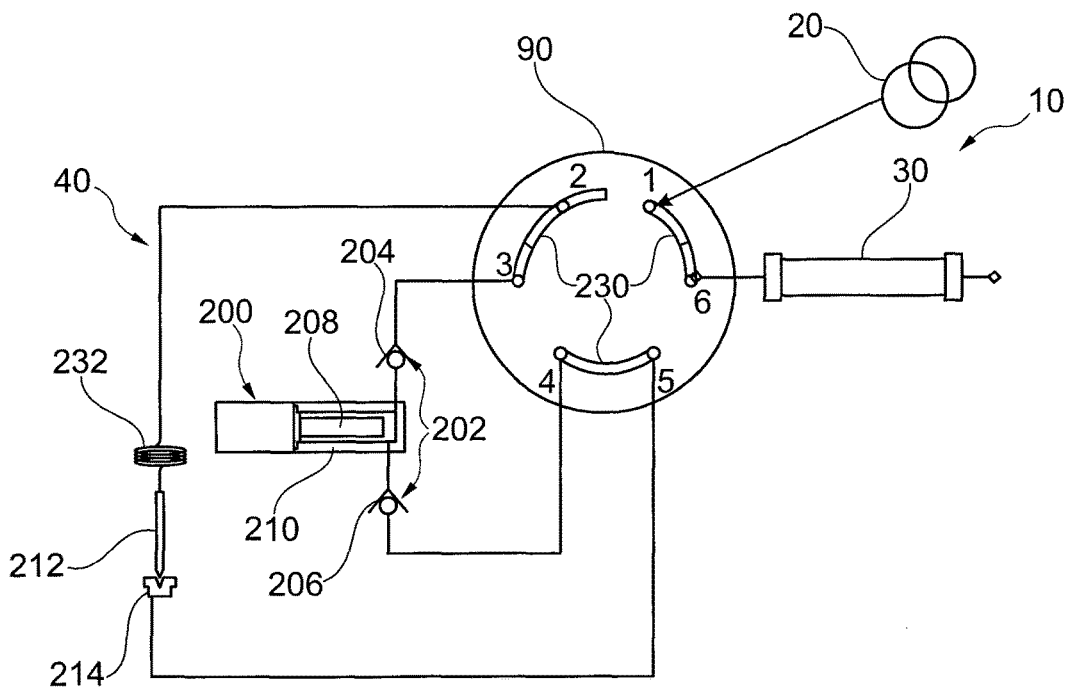
FIG. 6 shows a sample injector according to another exemplary embodiment in an operating mode.
Figure 7:
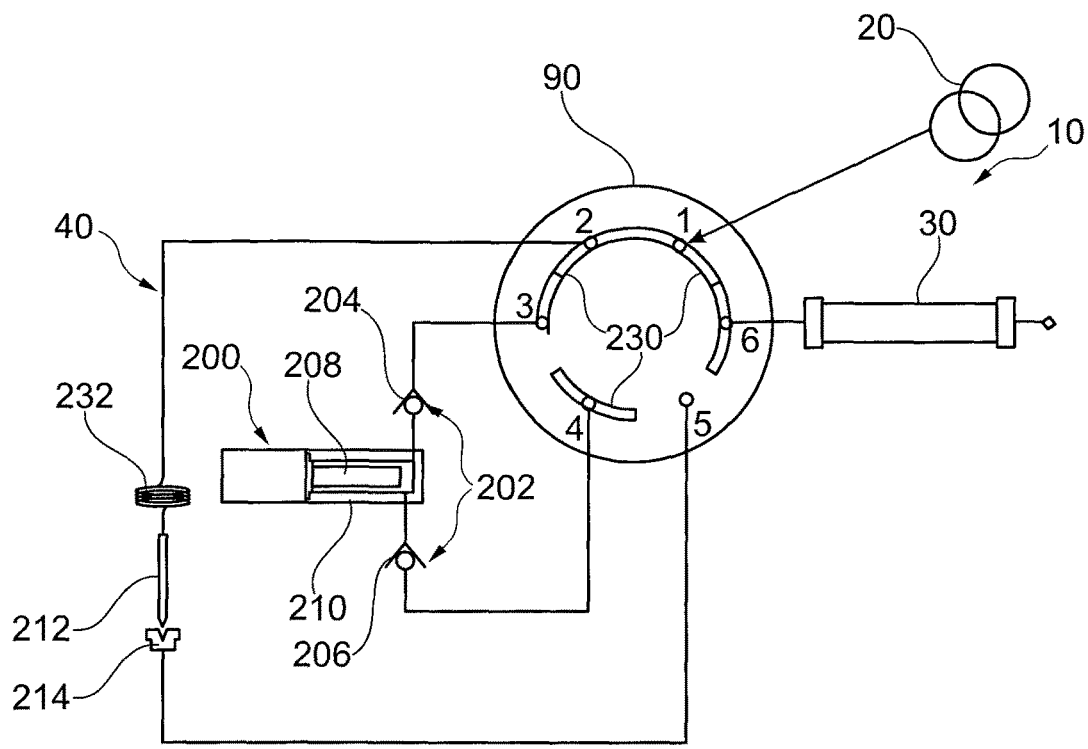
FIG. 7 shows the sample injector illustrated in FIG. 6 in another operating mode.
Figure 8:
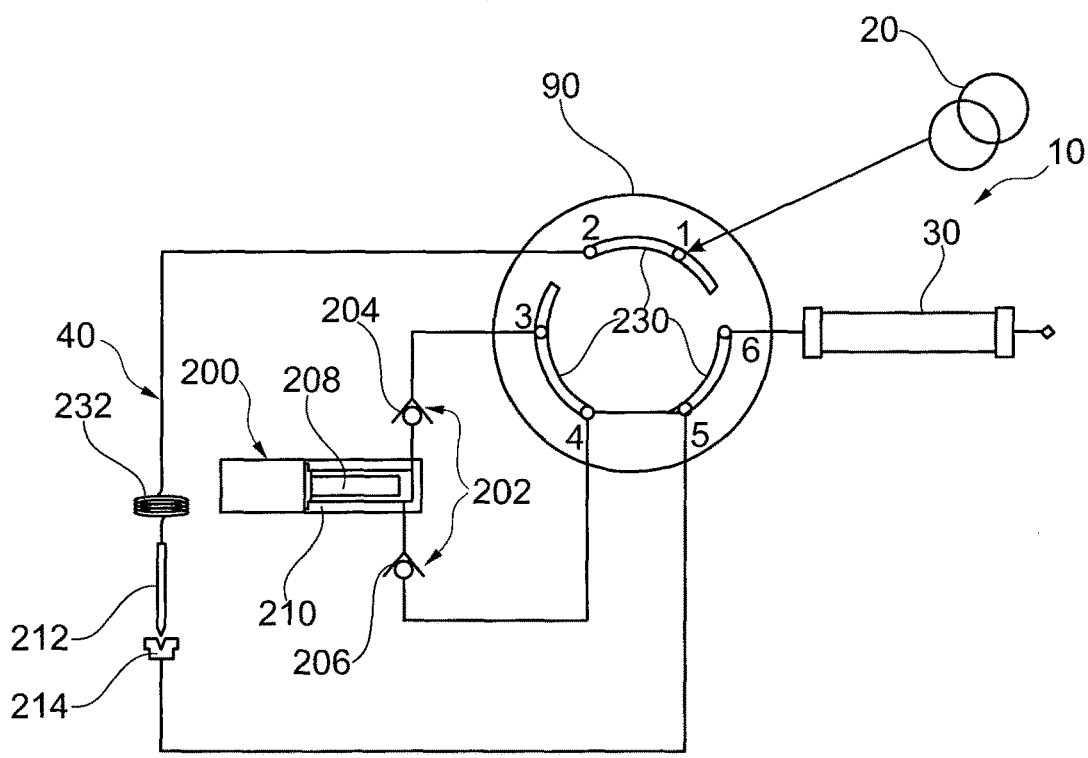
FIG. 8 shows the sample injector illustrated in FIG. 6 in another operating mode.

FIG. 6 to FIG. 8 show a sample injector 100 according to another exemplary embodiment in different operation modes.

According to FIG. 6 to FIG. 8, the injector valve 90 is switchable for operating the sample injector 40 in a mobile phase splitting mode in which mobile phase driven by the mobile phase drive 20 is split at the injector valve 90 partially towards the separation unit 30 and partially towards the metering device 200 (see FIG. 7). In the embodiment shown in FIG. 6 to FIG. 8, the operation mode shown in FIG. 6 corresponds to the operation mode shown in FIG. 3. In the operation mode according to FIG. 7, a flow split of mobile phase transported by the mobile phase drive 20 is accomplished. At port 1, this flow is split into a first portion which is directed towards separation unit 30 and in a second portion which is directed towards the metering device 200. Hence, the operation mode of FIG. 7 can be denoted as a drainage purge metering device operation mode. The amount or portion of fluid split into the path of the metering device 200 can be defined by a mutual cooperation or synchronization of the operation of the metering device 200 and the mobile phase drive 20. The operation mode of FIG. 8 corresponds to the operation mode of FIG. 2.

Figure 9:
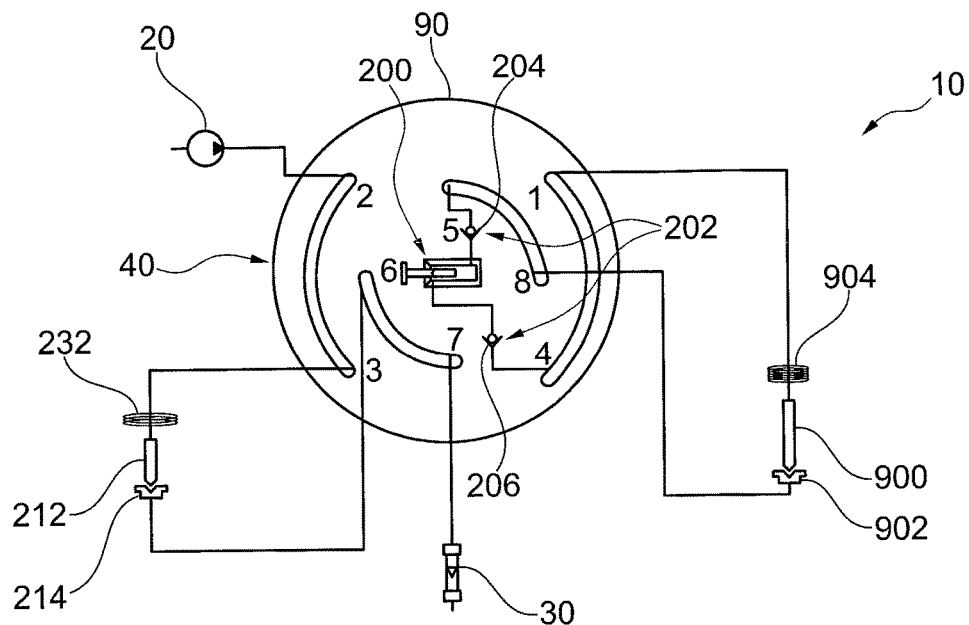
FIG. 9 shows a sample injector according to still another exemplary embodiment an operating mode.
Figure 10:
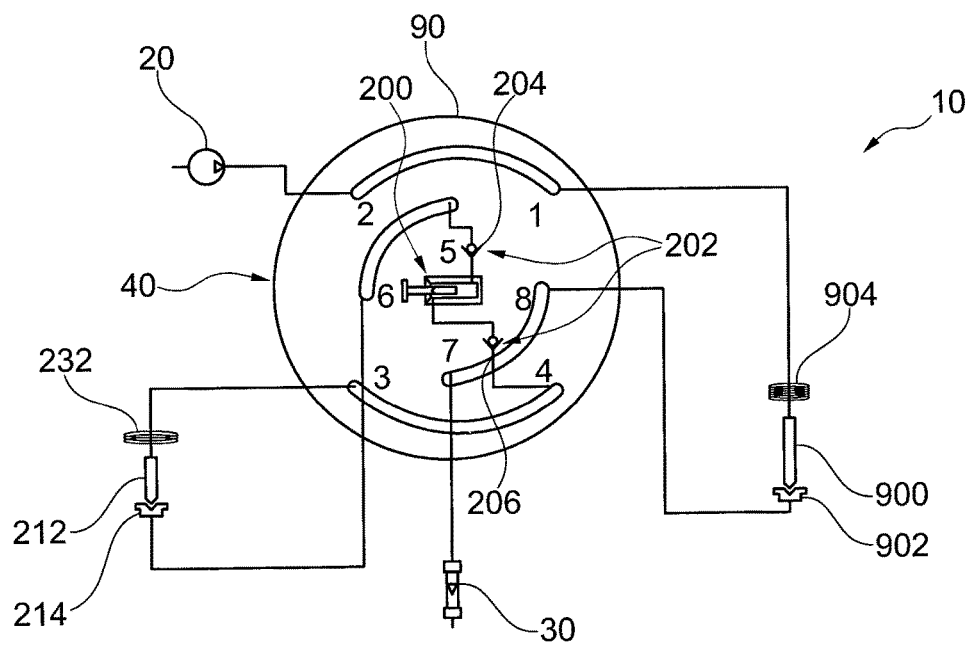
FIG. 10 shows the sample injector illustrated in FIG. 9 in another operating mode.

FIG. 9 and FIG. 10 show a sample injector 100 according to still another exemplary embodiment in different operation modes.

The sample injector 40 shown in FIG. 9 and FIG. 10 comprises a further needle 900 which is movable into a sample container 500 for intaking further sample fluid while other sample fluid previously intaken via the other needle 212 is separated in the separation mode. Moreover, the further needle 900 is movable into a further seat 902 in fluid communication with the injector valve 90 for driving the intaken further sample fluid between the mobile phase drive 20 and the separation unit 30 for separation so that while one of the needle 212 and the further needle 900 is arranged in a fluidic path between the mobile phase drive 20 and the separation unit 30, the respective other needle 900, 212 is operable for intaking sample fluid.

FIG. 9 and FIG. 10 hence show the corresponding sample separation apparatus 10 and sample injector 40 in a dual needle configuration in which two needles 212, 900 and corresponding seats 214, 902 are both served and operated alternatingly by a common injector valve 90, metering device 200 and flow direction controller 202. In each operation mode, previously intaken sample fluid in one of sample loops 232, 904 is separated in the separation unit 30 using mobile phase pumped by the mobile phase drive 20. Simultaneously, new sample fluid can be intaken via the respectively other needle 212, 902 and the respectively other sample loop 232, 904. Therefore, the throughput of sample fluid can be significantly reduced with the configuration according to FIG. 9 and FIG. 10 as compared to a single needle approach. In terms of flow direction control no additional hardware effort is required. According to FIG. 9, sample fluid in the sample loop 232 is presently injected between the mobile phase drive 20 and the separation unit 30 for separation thereof, while new sample fluid may be intaken via the needle 902 into sample loop 904. In the operation mode according to FIG. 10 and the corresponding switching mode of the injector valve 90, sample fluid injected according to FIG. 9 into the sample loop 904 can be separated by the mobile phase drive 20 in cooperation with the separation unit 30. At the same time, further new sample fluid can be intaken via the needle 212 into the sample loop 232.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A sample injector configured to introduce a sample fluid into a mobile phase, wherein the mobile phase is driven by a mobile phase drive through a separation unit for separating compounds of the sample fluid in the mobile phase, the sample injector comprising:
 a metering device comprising an inlet for intaking fluid and an outlet for discharging fluid;
 a sample flow line comprising a first end, a second end, and a sample loop between the first end and the second end; and
 an injector valve being switchable for operating the sample injector selectively in:
 a first mode, in which the first end of the sample flow line is coupled to the inlet of the metering device, the second end of the sample flow line is coupled to the outlet of the metering device, and the mobile phase drive is coupled to the separation unit; and a second mode, in which the first end of the sample flow line is coupled to the mobile phase drive and the second end of the sample flow line is coupled to the separation unit.

2. The sample injector of claim 1, wherein the flow direction controller comprises one of a first flow direction valve and a flow restrictor arranged between the metering device and a first port of the injector valve.

3. The sample injector of claim 1, wherein the flow direction controller comprises a second flow direction valve arranged between the metering device and a second port of the injector valve.

4. The sample injector of claim 2, wherein at least one of the first flow direction valve and the second flow direction valve is configured as a passive valve, in particular a non-return valve, more particularly a non-return ball valve.

5. The sample injector of claim 4, wherein the metering device comprises a piston movable in a piston chamber for displacing fluid, wherein piston backward motion enables fluid flow through the first flow direction valve while disabling fluid flow through the second flow direction valve, and piston forward motion enables fluid flow through the second flow direction valve while disabling fluid flow through the first flow direction valve.

6. The sample injector of claim 4, wherein at least one of the first flow direction valve and the second flow direction valve is one of a valve biased into a fluid disabling mode by a biasing element, in particular one of a biasing weight and a biasing spring, more particularly one of a helical spring and a flat spring.

7. The sample injector of claim 2, comprising a control unit configured for controlling a switching state of at least one of the first flow direction valve and the second flow direction valve to thereby define at least one of the enabled flow direction and the disabled flow direction.

8. The sample injector of claim 3, wherein the first flow direction valve and the second flow direction valve are configured so that, while one of them is in a fluid flow disabling mode, the respectively other one is in a fluid flow enabling mode.

9. The sample injector of claim 3, wherein, in the separation mode, the first flow direction valve and the second flow direction valve are fluidically coupled to one another via the injector valve.

10. The sample injector of claim 1, wherein the metering device is configured for depressurizing a fluidic path in which the metering device is located before switching into the sample intake mode.

11. The sample injector of claim 1, wherein the metering device is configured for prepressurizing a fluidic path in which the metering device is located before switching into the separation mode.

12. The sample injector of claim 1, wherein the injector valve is switchable for operating the sample injector in a mobile phase splitting mode in which mobile phase driven by the mobile phase drive is split at the injector valve partially towards the separation unit and partially towards the metering device.

13. The sample injector of claim 1, wherein the metering device is located outside of a flow path between the mobile phase drive and the separation unit in both the separation mode and the sample intake mode, in particular in each operation mode of the sample injector.

14. The sample injector of claim 1, comprising a needle which is movable into a sample container in the sample intake mode, and which is movable into a seat in fluid communication with the injector valve in the sample separation mode.

15. The sample injector of claim 14, wherein the metering device is controllable for moving a piston of the metering device multiple times forwardly and backwardly in the sample intake mode while the needle remains in the sample container to thereby intake multiple quantities of the sample fluid during the multiple backward motions of the piston.

16. The sample injector of claim 14, wherein the metering device is controllable for moving a piston of the metering device forwardly when the needle is out of fluid communication with the mobile phase drive, in particular when the needle is outside of the seat, to thereby backflush the seat.

17. The sample injector of claim 14, comprising a further needle which is movable into a sample container for intaking further sample fluid while other sample fluid previously intaken is separated in the separation mode, and which further needle is movable into a further seat in fluid communication with the injector valve for driving the intaken further sample fluid between the mobile phase drive and the separation unit for separation so that, while one of the needle and the further needle is arranged in a fluidic path between the mobile phase drive and the separation unit the respective other needle is operable for intaking sample fluid.

18. A fluid separation apparatus for separating compounds of a sample fluid in a mobile phase, the fluid separation apparatus comprising:

a mobile phase drive, particularly a pumping system, configured to drive the mobile phase through the fluid separation apparatus;

a sample injector of claim 1 configured to introduce the sample fluid into the mobile phase; and a separation unit, particularly a chromatographic column, configured for separating the compounds of the sample fluid in the mobile phase.

19. The fluid separation apparatus of claim 18, further comprising at least one of:

a detector configured to detect separated compounds of the sample fluid;

a collection unit configured to collect separated compounds of the sample fluid;

a data processing unit configured to process data received from the fluid separation apparatus;

a degassing apparatus for degassing the mobile phase.

20. A method of operating a sample injector to introduce a sample fluid into a mobile phase, wherein the mobile phase is to be driven by a mobile phase drive through a separation unit for separating compounds of the sample fluid in the mobile phase, wherein the method comprises:

switching an injector valve into a sample intake mode in which a metering device for displacing fluid is operated to intake a metered amount of a sample fluid from a sample container into the sample injector;

subsequently switching the injector valve into a separation mode in which the intaken sample fluid is driven by the mobile phase drive for separating the compounds by the separation unit;

at least during the sample intake mode, providing a flow of fluid displaced by the metering device along a defined flow direction and disabling a flow of fluid in an opposite flow direction, wherein the injector valve switches to operate the sample injector selectively in:

a first mode, in which the first end of the sample flow line is coupled to the inlet of the metering device, the second end of the sample flow line is coupled to the outlet of the metering device, and the mobile phase drive is coupled to the separation unit; and a second mode, in which the first end of the sample flow line is coupled to the mobile phase drive and the second end of the sample flow line is coupled to the separation unit.

* * * * *